US008821560B2

(12) United States Patent
Yoon et al.

(10) Patent No.: US 8,821,560 B2
(45) Date of Patent: Sep. 2, 2014

(54) OPTICAL STIMULUS PROBE STRUCTURE WITH OPTICAL TRANSMITTABLE PROBE AND MANUFACTURING METHOD THEREOF

(75) Inventors: Eui Sung Yoon, Seoul (KR); Il Joo Cho, Seoul (KR); Jin Seok Kim, Seoul (KR); Kyoung Hwan Na, Uiwang-si (KR); Hyung Dal Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 203 days.

(21) Appl. No.: 13/160,377

(22) Filed: Jun. 14, 2011

(65) Prior Publication Data

US 2012/0172952 A1 Jul. 5, 2012

(30) Foreign Application Priority Data

Jan. 5, 2011 (KR) ........................ 10-2011-0000875

(51) Int. Cl.
*A61N 5/06* (2006.01)

(52) U.S. Cl.
CPC ....... *A61N 5/0622* (2013.01); *A61N 2005/0612* (2013.01); *A61N 2005/0651* (2013.01)
USPC ............................................................ 607/92

(58) Field of Classification Search
USPC ..................................................... 607/88–94
See application file for complete search history.

(56) References Cited

U.S. PATENT DOCUMENTS

| | | | | |
|---|---|---|---|---|
| 6,564,087 | B1 | 5/2003 | Pitris et al. | |
| 7,116,886 | B2 * | 10/2006 | Colgan et al. | 385/137 |
| 2010/0114190 | A1 * | 5/2010 | Bendett et al. | 607/3 |

FOREIGN PATENT DOCUMENTS

| | | | |
|---|---|---|---|
| EP | 1405608 | A1 | 4/2004 |

* cited by examiner

*Primary Examiner* — Bill Thomson
*Assistant Examiner* — John R Downey
(74) *Attorney, Agent, or Firm* — Fenwick & West LLP

(57) ABSTRACT

Disclosed are an optical stimulation probe structure having a probe body inserted into a subject, a fixing body that fixes the probe body and a light radiator that transmits an optical signal to the probe body, wherein the probe body is made of an optical transmission material capable of transmitting an optical signal, such that the optical signal transmitted from the light radiator is transmitted through the probe body to the subject, and a method for manufacturing the same.

8 Claims, 4 Drawing Sheets

100
130
131
121
120
110
111
112
111

OPTICAL STIMULUS PROBE STRUCTURE WITH OPTICAL TRANSMITTABLE PROBE AND MANUFACTURING METHOD THEREOF

CROSS-REFERENCE TO RELATED APPLICATIONS

This application claims priority under 35 U.S.C. §119 to Korean Patent Application No. 10-2011-0000875, filed on Jan. 5, 2011, in the Korean Intellectual Property Office, the disclosure of which is incorporated herein by reference in its entirety.

TECHNICAL FIELD

The present disclosure relates to an optical stimulation probe structure and a method for manufacturing the same. More particularly, the disclosure relates to an optical stimulation probe structure equipped with an optical transmittable probe and a method for manufacturing the same.

BACKGROUND

Recently, studies are actively carried out to understand brain functions and treat brain diseases by stimulating cranial nerves of a subject and detecting and analyzing signals in response thereto.

In order to directly stimulate the cranial nerves of the subject and acquire information therefrom, a neural probe that can be inserted into the body of the subject is used. Also, a microminiature neural probe with an electrode array integrated was developed to detect as much information as possible.

In general, existing neural probes apply electrical stimulus to the cranial nerves by using electrodes arranged on the probe body. However, the application of electrical stimulus to the cranial nerves may damage the cranial nerves. In addition, since the brain is composed of electrically conducting matter, it is impossible to locally stimulate a desired site.

Thus, application of optical stimulus to the cranial nerves and collection of response signals thereto are preferred recently.

Generally, an optical stimulation probe for applying the optical stimulus is composed of a silicon probe body with an optical fiber attached thereto for insertion into the brain, which makes precise control of the stimulation site difficult and is inevitably accompanied by large probe size.

In this regard, a neural probe with an optical waveguide for optical transmission was proposed. However, the procedure for manufacturing the probe is very complicated and the probe structure is also complex.

SUMMARY

The present disclosure is directed to providing an optical stimulation probe structure that can be manufactured simply and is capable of effectively stimulating a desired site because of simple structure and small size.

In one general aspect, the present disclosure provides an optical stimulation probe structure including: a probe body inserted into a subject; a fixing body that fixes the probe body; and a light radiator that transmits an optical signal to the probe body, wherein the probe body is made of an optical transmission material capable of transmitting an optical signal, such that the optical signal transmitted from the light radiator is transmitted through the probe body to the subject.

The optical transmission material may be glass or a polymer capable of transmitting an optical signal.

The light radiator may be an optical fiber that transmits an optical signal from an external light source.

A groove in which the optical fiber can be seated may be formed on the fixing body.

An electrode capable of collecting a response signal from the subject may be formed on the probe body, and an electrical conductor electrically connected to the electrode may be arranged on the fixing body.

The fixing body may be formed of silicon.

In another general aspect, the present disclosure provides a method for manufacturing an optical stimulation probe structure including a probe body inserted into a subject, a fixing body to which the probe body is attached, and a light radiator that transmits an optical signal to the probe body, wherein the probe body is made of an optical transmission material capable of transmitting an optical signal, such that the optical signal transmitted from the light radiator is transmitted through the probe body to the subject, including: forming a silicon layer; forming a glass layer on the silicon layer; polishing the glass layer to a desired thickness; removing the glass layer such that only the shape of the probe body remains and thereby forming the probe body; integrating an electrode and an electrical conductor on the probe body; forming a groove in which the light radiator is seated on the silicon layer; and partly removing the portion of the silicon layer located below the probe body and forming the fixing body that fixes the rear end of the probe body.

In another general aspect, the present disclosure provides a method for manufacturing an optical stimulation probe structure including a probe body inserted into a subject, a fixing body to which the probe body is attached, and a light radiator that transmits an optical signal to the probe body, wherein the probe body is made of an optical transmission material capable of transmitting an optical signal, such that the optical signal transmitted from the light radiator is transmitted through the probe body to the subject, including: forming a silicon layer; etching the upper portion of the silicon layer to form a pattern having the shape of the probe body; molding a polymer capable of transmitting an optical signal into the pattern to form the probe body; integrating an electrode and an electrical conductor on the probe body; forming a groove in which the light radiator is seated on the silicon layer; and partly removing the portion of the silicon layer located below the probe body and forming the fixing body that fixes the rear end of the probe body.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which.

Figure 1:
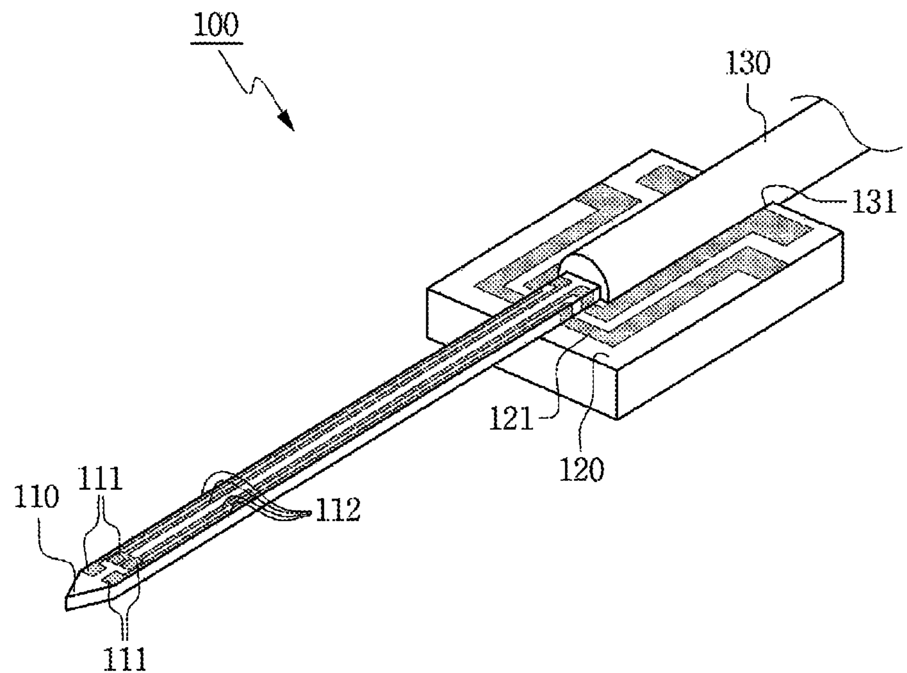
FIG. 1 is a perspective view of an optical stimulation probe structure according to an embodiment of the present disclosure.

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

In the figures, reference numerals refer to the same or equivalent parts of the disclosure throughout the several figures of the drawings.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of the example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

Embodiment 1

FIG. 1 is a perspective view of an optical stimulation probe structure 100 according to an embodiment of the present disclosure.

Referring to FIG. 1, the optical stimulation probe structure 100 according to this embodiment comprises a probe body 110, a fixing body 120 and a light radiator 130.

The probe body 110 is inserted into the body of a subject, e.g. a mouse. Its front end is pointed such that it can be easily inserted into the body of the subject. The rear end of the probe body 110 is fixed to the fixing body 120.

An electrode array 111 capable of collecting a response signal from the subject and an electrical conductor 112 electrically connected to the electrode array 111 are arranged on the probe body 110.

The electrical conductor 112 is electrically connected to an electrical conductor 121 arranged on the fixing body 120. The electrical conductor 121 arranged on the fixing body 120 is electrically connected to the wiring of a printed circuit board (PCB, not shown) to which the fixing body 120 is attached.

In this configuration, the response signal from the subject is collected by the electrode array 111 of the probe body 110, and the collected response signal is transmitted to outside via the electrical conductors 112, 121.

According to this embodiment, the probe body 110 is made of an optical transmission material capable of transmitting an optical signal. Specifically, the probe body 110 is made of glass, which is an optical transmission material.

The light radiator 130 is arranged at the rear end of the probe body 110 in order to transmit the optical signal to the probe body 110.

In this embodiment, an optical fiber that transmits an optical signal from an external light source (not shown) is used as the light radiator 130.

The optical fiber 130 is arranged to extend along a length direction of the probe body 110 such that the optical signal can be transmitted via the probe body 110. The arranged optical fiber 130 is attached and fixed to the fixing body 120.

In a probe structure that stimulates the nerves of a subject through optical stimulation, a light radiator that transmits or generates an optical signal and a member that receives the optical signal need to be arranged for efficient transmission of the optical signal. Furthermore, the light radiator needs to be fixed rigidly while the probe structure is being used.

According to this embodiment, a groove 131 is formed on the fixing body 120 so as to stably fix the optical fiber 130 to the fixing body 120 and ensure stable arrangement of the probe body 110 which receives the optical signal.

As shown in FIG. 1, the groove 131 is formed to come into contact with the rear end of the probe body 110, and the optical fiber 130 is seated in the groove 131.

The groove 131 allows easy arrangement of the optical fiber 130 having a larger diameter than the probe body 110 on the probe body 110, and ensures stable fixing of the optical fiber 130 to the fixing body 120.

Although the optical fiber 130 capable of transmitting an optical signal from an external light source is used as the light radiator in this embodiment, it is only exemplary. For example, a light source such as a light-emitting diode (LED) may be directly fixed to the fixing body 120 so as to transmit an optical signal to the probe body 110. That is to say, as long as the optical signal can be transmitted to the probe body 110, not just a member that transmits an optical signal from an external light source but also the light source itself, which directly generates light, may be employed as the light radiator according to this embodiment.

The optical stimulation probe structure 100 according to this embodiment allows analysis of response signal from the nerves of the subject by stimulating the nerves and collecting the response signals thereto.

For this, the probe body 110 is inserted into the test site, e.g. brain, of the subject. With the probe body 110 inserted, an optical signal is applied to the probe body 110 using the light radiator 130. The applied optical signal is transmitted via the probe body 110 to the subject, and applies optical stimulus to the nerves of the subject. The nerves of the subject generate a signal in response to the applied optical stimulus, and the generated response signal is collected by the electrode array 111 arranged on the probe body 110. The response signal information collected at the electrode array 111 is transmitted to the PCB via the electrical conductors 112, 121 and received by an external computer. The received response signal information may be used to analyze, for example, the neuronal operation of the subject.

According to this embodiment, since the probe body 110 is made of glass capable of transmitting light, the optical signal can be transmitted without having to provide an additional optical waveguide on the probe body 110. Thus, the probe structure may have a simple structure and a small size. In addition, since the electrode array 111 is integrated at the front end of the probe body 110, all the signals coming from the nerves near the inserted probe body 110 may be detected.

Since glass is heat-resistant, its shape is not deformed even when a high-power optical signal is radiated. Further, due to small optical loss, the loss of light during the transmission of the optical signal via the probe body 110 is greatly reduced.

Hereinafter, a method for manufacturing the optical stimulation probe structure 100 according to this embodiment will be described in reference to FIGS. 2A to 2F.

FIGS. 2A to 2F show a process of manufacturing the optical stimulation probe structure 100 according to this embodiment.

According to this embodiment, the probe body 110 is made of glass, and the fixing body 120 that fixes the probe body 110 is made of silicon.

Figure 2A:
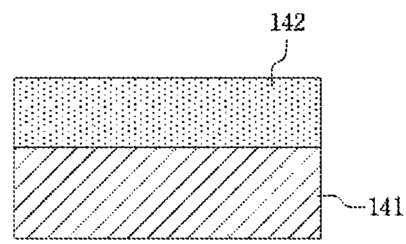
FIGS. 2A to 2F show a process of manufacturing the optical stimulation probe structure shown in FIG. 1.

To prepare the probe body 110 and the fixing body 120, a silicon layer 141 is formed first, and then a glass layer 142 is formed on the silicon layer 141 (FIG. 2A).

Figure 2B:
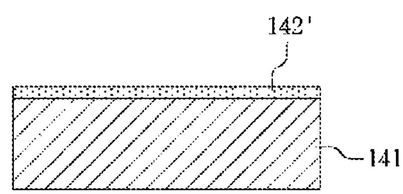

Since the probe body 110 should be easily inserted into the subject, it needs to be as thin as possible. According to this embodiment, in order to reduce the thickness of the probe body 110, the glass layer 142 is polished to form a glass layer 142' with a desired thickness (FIG. 2B).

Figure 2C:
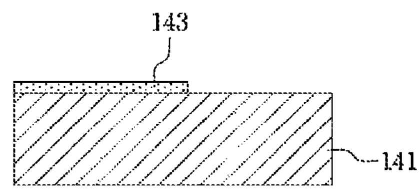
Figure 2D:
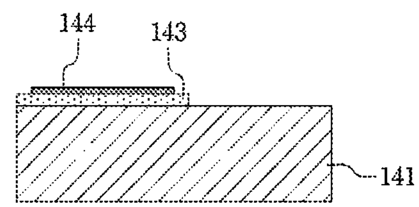

Then, the glass layer 142' is etched and partly removed such that only the shape of the probe body 110 remains (FIG. 2C). Subsequently, an electrode array, an electrical conductor 144, etc. are integrated on the remaining glass layer 143 (FIG. 2D).

Figure 2E:
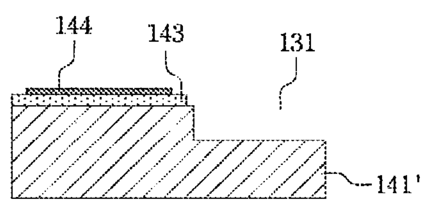

Next, the groove 131 is formed at the rear end of the glass layer 143 through etching (FIG. 2E). The depth and height of the groove 131 are adjusted adequately considering, for example, the diameter of the optical fiber, so that the optical fiber is arranged well on the glass layer 143, i.e. the probe body 110, such that the optical signal is transmitted well to the probe body 110.

Figure 2F:
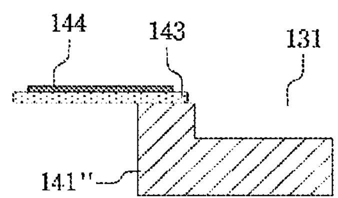

Finally, the portion of the silicon layer 141' located below the glass layer 143, which has the shape of the probe body 110, is partly removed, such that a silicon layer 141" is formed. Only the rear end of the probe body 110 is fixed to the silicon layer 141". As a result, the fixing body 120 is completed (FIG. 2F).

After the optical fiber is seated in the groove 131 of the structure and fixed using, for example, glue, the electrical conductor 121 is wired on the fixing body 120 to electrically connect with the electrical conductor 144 on the probe body 110. Then, the optical stimulation probe structure 100 according to this embodiment is completed.

If the fabricated optical stimulation probe structure 100 is attached and electrically connect to the PCB, it is ready to collect response signals to optical simulation.

Since the optical stimulation probe structure 100 according to this embodiment can be manufactured without having to provide an additional optical waveguide on the probe body 110, the associated manufacturing process is simple.

Embodiment 2

Figure 3:
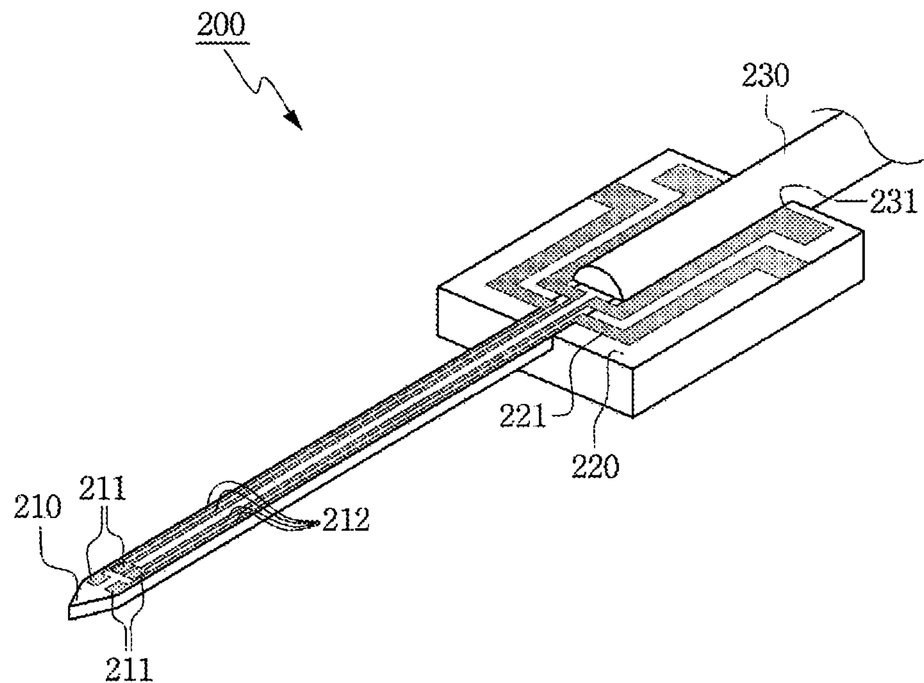
FIG. 3 is a perspective view of an optical stimulation probe structure according to another embodiment of the present disclosure.

FIG. 3 is a perspective view of an optical stimulation probe structure 200 according to another embodiment of the present disclosure.

Referring to FIG. 3, the optical stimulation probe structure 200 according to this embodiment comprises a probe body 210, a fixing body 220 and a light radiator 230.

The probe body 210 according to this embodiment is made of an optical transmission material capable of transmitting an optical signal. Specifically, the probe body 210 is made of a polymer capable of transmitting light.

Examples of the polymer capable of transmitting light include PMMA, PS, PPDMS, SU-8, COC, etc., but are not limited thereto.

Since the configuration of the optical stimulation probe structure 200 is substantially the same as that of the optical stimulation probe structure 100 according to Embodiment 1 except that the probe body 210 is made of the polymer capable of transmitting light, a detailed description thereof will be omitted.

Hereinafter, a method for manufacturing the optical stimulation probe structure 200 according to this embodiment will be described in reference to FIGS. 4A to 4F.

FIGS. 4A to 4F show a process of manufacturing the optical stimulation probe structure 200 according to this embodiment.

According to this embodiment, the probe body 210 is made of a polymer capable of transmitting light, and the fixing body 220 that fixes the probe body 210 is made of silicon.

Figure 4A:
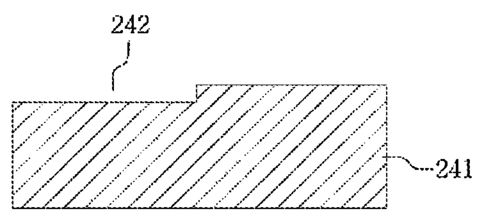
FIGS. 4A to 4F show a process of manufacturing the optical stimulation probe structure shown in FIG. 3.

To prepare the fixing body 220, a silicon layer 241 is formed first, and then the upper portion of the silicon layer 241 is etched to form a having the shape of the probe body 210 (FIG. 4A).

Figure 4B:
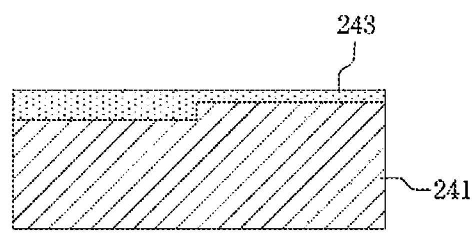
Figure 4C:
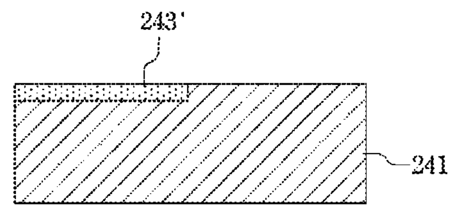

Then, a melt polymer is poured into the pattern 242 and then cooled to mold into the shape of the probe body 210 (FIG. 4B). If necessary, the unnecessary portion other than the shape of the probe body 210 may be removed by polishing such that only the shape of the probe body 210 remains on the pattern 242 (FIG. 4C).

Figure 4D:
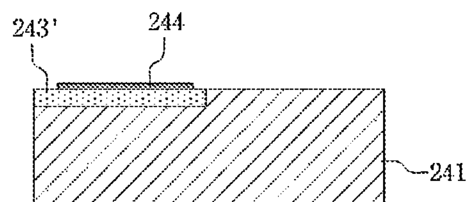

Subsequently, an electrode array, an electrical conductor 244, etc. are integrated on the remaining polymer layer 243' (FIG. 4D).

Figure 4E:
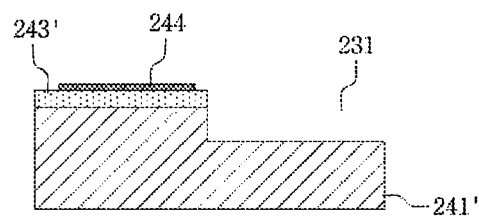

Next, a groove 231 is formed at the rear end of the polymer layer 243' through etching (FIG. 4E). The depth and height of the groove 231 are adjusted adequately considering, for example, the diameter of the optical fiber, so that the optical fiber is arranged well on the polymer layer 243', i.e. the probe body 210, such that the optical signal is transmitted well to the probe body 210.

Figure 4F:
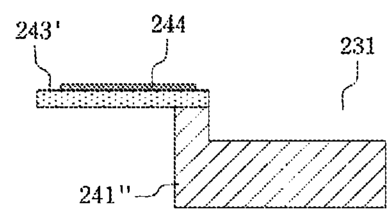

Finally, the portion of the silicon layer 241' located below the polymer layer 243', which has the shape of the probe body 210, is partly removed, such that silicon layer 241" is formed. Only the rear end of the probe body 210 is fixed to the silicon layer 241". As a result, the fixing body 220 is completed (FIG. 4F).

After the optical fiber is seated in the groove 231 of the structure and fixed using, for example, glue, the electrical conductor 221 is wired on the fixing body 220 to electrically connect with the electrical conductor 244 on the probe body 210. Then, the optical stimulation probe structure 200 according to this embodiment is completed.

According to this embodiment, since the probe body 210 is made of the polymer capable of transmitting light, the optical signal can be directly transmitted to the probe body 210 without having to provide an additional optical waveguide on the probe body 210. Hence, it is possible to manufacture a probe structure having a simple structure and a small size.

Further, by using the polymer that can be molded, the optical stimulation probe structure 200 can be manufactured through a very simple process, and the manufactured probe body 210 is resistant to heat. In addition, even when a high-power optical signal is radiated, the shape of the probe body 210 is not deformed. Furthermore, due to small optical loss, the loss of light during the transmission of the optical signal is greatly reduced.

Since the optical stimulation probe structure according to the present disclosure directly transmits the optical signal via the probe body, there is no need of providing an additional optical waveguide. Thus, the probe structure has a simple structure and a small size.

Also, since the nerves of the subject is stimulated optically, not electrically, for collecting information, it is possible to locally stimulate the desired site without damaging the nerves.

While the present disclosure has been described with respect to the specific embodiments, it will be apparent to those skilled in the art that various changes and modifications may be made without departing from the spirit and scope of the disclosure as defined in the following claims.

What is claimed is:

1. An optical stimulation probe comprising:

a probe body configured for transmission of an optical signal, the probe body including:

an optically transparent layer;

an electrode array disposed on an outer surface at a first end of the optically transparent layer; and at least one first electrical conductor electrically connected to the electrode array and disposed on the outer surface from the first end to a second end of the optically transparent layer;

a fixing body that fixes the second end of the optically transparent layer, the fixing body comprising:

a semiconducting layer; and at least one second electrical conductor disposed on a surface of the semiconducting layer and electrically connected to the at least one first electrical conductor; and a light radiator configured to transmit the optical signal to the second end of the optically transparent layer of the probe body, the optical signal further propagated from the second end to the first end of the optically transparent layer.

2. The optical stimulation probe according to claim 1, wherein the optically transparent layer is glass.

3. The optical stimulation probe according to claim 1, wherein the optically transparent layer is a polymer capable of transmitting an optical signal.

4. The optical stimulation probe according to claim 1, wherein the light radiator is an optical fiber that transmits the optical signal from an external light source.

5. The optical stimulation probe according to claim 4, wherein a groove in which the optical fiber can be seated is formed on the fixing body.

6. The optical stimulation probe according to claim 1, wherein the semiconducting layer of the fixing body is formed of silicon.

7. A method for manufacturing an optical stimulation probe, the method comprising:

forming a silicon layer of a fixing body;

integrating an electrical conductor on an outer surface of the silicon layer of the fixing body;

depositing a glass layer on the silicon layer;

polishing the glass layer to a desired thickness;

forming a probe body by removing a portion of the glass layer;

integrating an electrode array on an outer surface of the probe body at a first end of the probe body;

integrating an electrical conductor on the outer surface of the probe body, the electrical conductor electrically connecting the electrode array at the first end of the probe body to the fixing body electrical conductor;

forming a groove in the silicon layer;

placing a light radiator in the groove of the silicon layer of the fixing body, the light radiator configured to transmit an optical signal into a second end of the probe body, the optical signal for propagating from the second end to the first end of the of the probe body; and partly removing the portion of the silicon layer located below the probe body and forming the fixing body that fixes the rear end of the probe body.

8. A method for manufacturing an optical stimulation probe, the method comprising:

forming a silicon layer of a fixing body;

etching an upper portion of the silicon layer of the fixing body to form a pattern having a shape of a rear end of a probe body;

molding an optically transparent polymer capable of transmitting an optical signal into the pattern to form the probe body;

integrating an electrode array on an outer surface of the probe body at a first end of the probe body;

integrating an electrical conductor on the outer surface of the probe body, the electrical conductor electrically connecting the electrode array at the first end of the probe body to an electrical conductor of the fixing body;

forming a groove in the silicon layer in which a light radiator is seated, the light radiator configured to transmit an optical signal into a rear end of the probe body, the optical signal propagating from the rear end to the first end of the of the probe body; and partly removing a portion of the silicon layer located below the probe body and forming the fixing body that fixes the rear end of the probe body.

* * * * *